United States Patent
Mani et al.

(10) Patent No.: US 6,315,988 B1
(45) Date of Patent: Nov. 13, 2001

(54) PROCESS FOR PREPARING PROTEIN-BOUND MELANIN AND/OR PEPTIDE BOUND MELANIN, AND PRODUCTS THEREOF

(75) Inventors: Indu Mani; Govindarajan Raman; Vandana Sharma, all of Bangalore (IN)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/663,007

(22) Filed: Sep. 15, 2000

Related U.S. Application Data

(63) Continuation-in-part of application No. 09/525,081, filed on Mar. 14, 2000.

(30) Foreign Application Priority Data

Mar. 17, 1999 (IN) .......................................... 193/BOM 199
May 4, 1999 (DE) .................................................... 9910274

(51) Int. Cl.⁷ ........................... A61K 7/44; A61K 7/135; A61K 7/021; C12P 1/00; C12N 1/14
(52) U.S. Cl. ................................ 424/60; 424/59; 424/62; 424/63; 435/41; 435/254.4
(58) Field of Search .................................. 424/60, 59, 62, 424/63; 426/250, 386; 435/41, 254.4

(56) References Cited

U.S. PATENT DOCUMENTS 4,278,656 * 7/1981 Nagai et al. .
4,515,773 * 5/1985 Herlihy .
5,216,116 * 6/1993 Pawelek .
5,384,116 * 1/1995 Pawelek et al. .

FOREIGN PATENT DOCUMENTS

WO 96/25920 * 8/1996 (WO) .

OTHER PUBLICATIONS

Kupper et al., Curr. Genet. 18: 331–335. Expression of tyrosinase in vegetative cultures of Neurospora crassa transformed with a metallothionein promoter/protyrosinase fusion gene, Nov. 1990.*

Kato et al., Biochimica et Biophysica Acta G, 881(3): 415–421. Tyrosinase–catalyzed of 3,4–dihydroxyphenylalanine with proteins through the sulfhydryl groups, 1986.*

Rosei et al., Biochimica et Biophysica Acta 1243(1): 71–7. Spectroscopic features of native and bleached melanins, Jan. 1995.*

* cited by examiner

Primary Examiner—Christopher R. Tate
Assistant Examiner—Michele C. Flood
(74) Attorney, Agent, or Firm—Milton L. Honig

(57) ABSTRACT

A process is provided for preparing protein- and/or peptide-bound melanin, which is soluble in an aqueous solution at pH 2 to 11 and temp 0° C. to 50° C., by the steps of reacting dihydroxyphenylalanine or tyrosine with an oxidant enzyme in the presence of an acidic protein and/or peptide having a pI of 3–6. The soluble protein- and/or peptide-bound melanin of this invention is useful as a sunscreen and as a coloring and/or flavoring for food.

8 Claims, No Drawings

PROCESS FOR PREPARING PROTEIN-BOUND MELANIN AND/OR PEPTIDE BOUND MELANIN, AND PRODUCTS THEREOF

This is a continuation-in part of Ser. No. 09/525,081 filed Mar. 14, 2000.

BACKGROUND OF THE INVENTION

1. Field of the Invention

The present invention relates to a process of producing melanin polymers in soluble form and to compositions including such polymers for providing sunscreen benefits by preventing and damaging effects of ultra-violet light on skin.

2. The Related Art

The treatment of human skin damaged through exposure to ultra-violet (UV) light, i.e. photo-damage, has been subject to much research effort in recent years, particularly with the realisation that skin cancer and other skin disorders can arise where the exposure to sunlight is excessive. The sensitivity of the human skin to UV exposure is dependent on the amount of the pigment melanin present in the skin.

The purpose of a sunscreen is to block the excessive UV radiation from affecting the skin. Sunscreens act by deflecting and scattering the incident light that produces burning and tanning of the skin or by absorbing this light. To prevent darkening of existing melanin in the skin, the skin has to be protected broadly across the UV range of about 320–400 nm. It is known that careful selection of sunscreens can offer this protection to the skin and reduce the darkening and damaging effects of the radiation.

WO 96/25920 (Yale University), describes the use of melanin polymers in cosmetic compositions for providing a substantive, natural appearing tan and to protect the skin from harmful effects of ultraviolet radiation. Since melanins absorb light throughout the ultraviolet and visible spectra, solubilized melanins also are effective as glass or plastic tinting agents for eye glasses, contact lenses, car windows, house windows, office buildings etc. Apart from cosmetic benefits, soluble melanins can also be used as colouring agents in coffee, tea, soda, whiskey and other liquors.

WO 92/16189 (Yale University), disclose compositions and methods for preparing soluble melanins stable at physiological pH and temperature. The method comprises reacting dopachrome and one or more enzymes derived from biological cells or tissues which have a pigmentary system. The melanin produced is soluble in an aqueous solution at a pH of at least 5 to 9 at a temperature of 0 to 100° C.

The commercial value of melanins that are soluble at physiological pH and temperature is very great. Soluble melanins occur in nature as isolated polymers or as bound to proteins.

It is an object of the present invention to provide a process for preparing solubilised forms of melanin bound to a peptide/protein with a pI in the range of 3 to 6. The melanin formed therein is soluble in an aqueous solution at pH 2 to 11 and temperature of 0° to 50.° C. The term pI refers to the negative of the log base 10 of the concentration of the protein peptide at the isoelectric point.

It is another object of the present invention to provide compositions comprising such melanin useful for providing sunscreen benefits by preventing the damaging effects of ultra-violet light on skin.

It is still another object of the present invention to provide compositions comprising such melanin useful for colouring and or flavouring foodstuffs such as coffee, tea, soda and other beverages.

SUMMARY OF THE INVENTION

Now it has been found that soluble melanin that is bound to protein in contrast to unbound melanin is particularly effective as a sunscreen, is more stable than the unbound variety and will not become degraded into toxic monomeric compounds. The soluble bound melanin of the present invention has hitherto not been achieved by known processes. Thus, it is another aspect of the present invention that a process is provided for generating a soluble bound melanin in good yield.

According to a first aspect of the present invention there is provided a process for preparing protein- and/or peptide-bound melanin, which is soluble in an aqueous solution at pH 2 to 11 and temperature 0° to 50° C., comprising the steps of reacting dihydroxyphenylalanine or tyrosine with an oxidant enzyme in the presence of an acidic protein and/or peptide having a pI of 3–6.

The reaction mixture may optionally additionally comprise one or more of the following; Dihydroxyindole, 5,6 dihydroxyindole-2-carboxylic acid, dopachrome, indole-5,6-quinone and/or melanochrome.

Preferably the enzyme is a naturally occurring oxidant enzyme such as a tyrosinase. Preferably the enzyme source is either *mushroom tyrosinase* or *neurospora crassa*. Amounts of the enzyme may range from about 0.001 to about 10, preferably from about 0.1 to about 1 $\mu$M (micro molar). This is equivalent to 15–150 Units of enzyme activity (1 Unit is defined as the amount of enzyme that will cause an increase in $A_{280}$ of 0.001 per min at pH 6.5 at 25° C., using L-Tyrosine as substrate).

The dihydroxyphenylalanine (DOPA) is preferably DL- or L-DOPA. Tyrosine is preferably in the L or DL configuration and may also encompass para, meta and ortho isomers around the phenyl ring. Amounts of the DOPA or tyrosine reactants may range in amounts from about 0.1 to about 10, but preferably from about 1 to 5 mM (milli molar). The proteins used should preferably have a molecular weight of at least 45,000 Da, more preferably from about 55,000 to about 100,000 Da, and a pI of 3–6. Suitable proteins include Bovine Serum Albumin and Ovalbumin for example. The concentration of protein used may be from about 1 $\mu$M to about 1 mM and is preferably from about 10–100 $\mu$M. The reaction mixture preferably contains DOPA, oxidant enzyme and the acidic protein/peptide in the ratio of about 1–5:0.0001–0.001:0.01–0.2 by molar ratio. Metal ions such as copper, zinc and iron may also be used to alter colour and properties of the melanin formed.

It is thought that the oxidant enzyme converts DOPA to dopaquinone and subsequently to dopachrome. At this stage, in the presence of oxygen and light, dopachrome is converted to a variety of intermediates such as dihydroxyindole, 5,6 dihydroxyindole-2-carboxylic acid, indole-5,6-quinone and/or melanochrome. The acidic proteins/peptides present in the reaction mixture assist in the polymerisation of these intermediates resulting in the formation of the soluble, protein-bound melanin of the present invention.

Although it is known in the art to use strong acids such as trichloroacetic acid with DOPA oxidation, it is more preferable to avoid the presence of trichloroacetic acid. By the absence of trichloroacetic acid is meant less than 1 ml but preferably less than 0.1 ml (10% trichloroacetic acid) per 0.1 mM DOPA, and optimally no trichloroacetic acid at all.

The invention also provides a soluble protein- and/or peptide-bound melanin obtainable by the process according to the first aspect of the present invention.

According to a further aspect of the present invention there is provided a sunscreen composition comprising:
(a) 0.1 to 10% by weight of the composition of the soluble, protein- and/or peptide-bound melanin of the present invention; and
(b) a cosmetically acceptable vehicle.

The present invention also provides a synergistic skin lightening composition comprising:
(a) from 0.1 to 10% by weight of the composition of a skin whitening agent and;
(b) 0.1 to 10% by weight of the composition of soluble, protein- and/or peptide-bound melanin.

The skin lightening caused by the composition of the invention is reversible and without any side effects.

Skin whitening agent may be chosen from niacin, niacinamide or a precursor thereof, extracts of placenta, hydroquinone and derivatives (eg. Arbutin), kojic acid, dicarboxylic acids (azelaic acid, sebacic acid), represented by the formula HOOC—(CxHy) —COOH where x=4 to 20 and y=6 to 40, ascorbic acid and derivatives thereof, hydroxy acids (lactic acid, glycolic acid, malic acid, tartaric acid etc), ferulic acid, retinol and derivatives, polyamino acid sequence with an isoelectric point (pI) between 2 to 5.5, organic sunscreens such as 4-tertiary butyl-4'-methoxy dibenzoylmethane, available under the trade name PARSOL 1789 from Givaudan, and/or 2-ethyl hexyl methoxy cinnamate, available under the trade name PARSOL MCX from Givauden or other UV A and UV B sunscreens and any other known skin whitening compounds.

The sunscreen and skin lightening composition, according to the invention can include cosmetically compatible carriers, preservatives, emulsifiers, thickeners, perfume, colour, skin benefit materials such as moisturisers, emollients antiageing compounds and other skin benefit agents.

The vehicle which forms part of the cosmetic composition is cosmetically acceptable in that it will not harm the skin. The vehicles that can be used in the compositions according to the invention can include powder absorbents, binders and carriers, and liquids such as emollients, propellants, solvents, humectants and thickeners, for example.

Moisturisers and humectants such as polyols, glycerol, cetyl alcohol, Carbopol® 934, ethoxylated castor oil, paraffin oils, lanolin and its derivatives may also be present.

Silicone compounds such as silicone surfactants like DC3225C (Dow Corning) and/or silicone emollients, silicone oil (DC-200 Ex-Dow Corning) can be used.

The compositions according to the invention can be prepared for topical application to the skin in the form of conventional products such as lotions, creams, ointments and aerosol products.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

Process for the Preparation of Soluble Protein Bound Melanin

The soluble melanin was prepared by reacting 5 mM of DL-DOPA and either 180 ug of tyrosinates (*Neurospora crassa*) or 10 ug of tyrosinase (Mushroom) (Equivalent to 20 U of tyrosinase) in a 0.125 M sodium acetate buffer pH 5.0, in a final volume of 1 ml. The acidic protein Bovine serum albumin (BSA) with pI 4.6 and a molecular weight 66,000 kD, at different concentrations (Table 1) was tested. The control sample was without the acidic protein. The samples were incubated for 12 hours at 25° C. and then centrifuged at 16,000×g for 10 minutes to pellet the melanin. The absorbance of the supernatant was measured at 500 nm (A 500 nm) to determine the level of soluble or non-pelletable melanin. The pellet was washed and sonicated in 1 ml distilled water and the absorbance measured at 500 nm to determine the level of pelletable melanin. The melanin prepared was also analysed for its properties.

TABLE 1

| Concentration BSA ($\mu$M) | Melanin (A 500 nm) | |
|---|---|---|
| | Pelletable | Soluble |
| 0 (Control) | 0.174 ± 0.022 | 0.055 ± 0.003 |
| 5 | 0.077 ± 0.010 | 0.290 ± 0.005 |
| 20 | 0.074 ± 0.004 | 0.320 ± 0.002 |

The data presented in Table 1 shows that in presence of an acidic protein the level of soluble melanin formed is significantly increased over control. The soluble melanin produced according to the invention is soluble in an aqueous solution at pH 2 to 11 and temperature 0° C. to 50° C. It is protein bound, and of a very high molecular weight (>100 KDa). It can be filtered through a 0.22 micron filter and remains in the soluble form when ultracentrifuged at 1,05,000×g for 1 hour. The soluble melanin is stable on acidification or alkalisation but gets precipitated on boiling. It can be lyophilised into a crystal form and redissolved in water. It varies in colour from golden brown to black and absorbs throughout the UV and visible wavelengths.

EXAMPLE 2

Effects of Different Proteins on the Formation of Soluble Protein Bound Melanin

The melanin preparation was done as described in example 1 but using proteins with different pI to determine the effect of acidic protein on the formation of soluble melanin. The proteins used are as described in Table 2.

TABLE 2

| Protein | pI | Concentration ($\mu$M) | Soluble Melanin |
|---|---|---|---|
| None | | | 0.055 |
| Proteinase K | 8.0 | 20 | 0.084 |
| BSA | 4.6 | 20 | 0.393 |
| Ovalbumin | 4.9 | 20 | 0.374 |

The data presented in Table 2 shows that the increase in the soluble melanin is due to the presence of an acidic protein and there is no corresponding increase when a basic protein (pI 8.0 ) was present.

EXAMPLE 3

Skin Lightening Composition According to the Invention

The invention will now be illustrated by reference to the following example of a cosmetic cream.

| Components | Weight (%) |
|---|---|
| Stearic acid | 15.0 |
| Cetyl alcohol | 0.5 |
| Dimethyl polysiloxane | 1.2 |
| Isopropyl palmitate | 4.4 |
| Glyceryl monostearate | 1.0 |
| Methyl/propyl paraben | 0.15 |
| Perfume | 0.2 |
| Niacinamide | 3.2 |
| Melanin | 1.5 |
| Water | To 100 |

EXAMPLE 4

Sunscreen Composition

This example illustrates a suncare cream incorporating the composition of the invention:

|  | Weight (%) |
|---|---|
| Melanin | 2 |
| Silicone oil 200 cts | 7.5 |
| Glycerylmonostearate | 3 |
| Cetostearyl alcohol | 1.6 |
| Polyoxyethylene-(20)-cetyl alcohol | 1.4 |
| Xanthan gum | 0.5 |
| Parsol ® 1789 | 1.5 |
| Octyl methoxycinnamate (Parsol ® MCX) | 7 |
| Perfume | Qs |
| Color | Qs |
| Water | To 100 |

EXAMPLE 5

A series of experiments were conducted to demonstrate the importance of pH and relative weight concentrations of reactants.

Experiments according to the present invention employed the following reactants: 5 mM DOPA (range tested=0.1–5 mM); 0.01 mM BSA (range tested=0.005–0.5 mM); and 40 µg tyrosinase (from Mushroom-Sigma; range tested=2–50 µg) in 1 ml of 0.125 mM sodium acetate buffer pH 5.0 or sodium phosphate buffer pH 7.0. Tubes were incubated overnight at room temperature. They were centrifuged at 14,000×g for 10 minutes to ensure complete removal of all particulate material. The supernatant obtained was black in colour and was referred to as "soluble melanin". Amounts were measured spectrophotometrically at O.D. 400 nm and quantitated using Sigma melanin as standard.

The experiments were repeated using all the concentration ranges of all the reactants. The results are reported in Tables 3 and 4.

TABLE 3

Soluble melanin formed (µg) at pH 5.0
using inventive method (tyrosinase concentration 40 µg)

| BSA (mM) | DOPA (mM) | | | | |
|---|---|---|---|---|---|
|  | 0.1 | 0.25 | 1.25 | 2.5 | 5 |
| 0.01 | 12.9 | 30.0 | 75.4 | 146.5 | 160.6 |
| 0.05 | 13.5 | 34.1 | 96 | 135.5 | 177.8 |
| 0.1 | 11.7 | 33.9 | 94.7 | 126.3 | 169.2 |
| 0.5 | 11.0 | 29.8 | 84.6 | 119.6 | 156.4 |

TABLE 4

Soluble melanin formed (µg) at pH 7.0
using inventive method (tyrosinase concentration 40 µg)

| BSA (mM) | DOPA (mM) | | | | |
|---|---|---|---|---|---|
|  | 0.1 | 0.25 | 1.25 | 2.5 | 5 |
| 0.01 | 46.0 | 108.5 | 376.5 | 486.2 | 602.1 |
| 0.05 | 50.3 | 115.3 | 347.0 | 464.2 | 600.9 |
| 0.1 | 49.4 | 119.6 | 345.8 | 477.0 | 575.8 |
| 0.5 | 45.4 | 105.5 | 276.5 | 365.4 | 580.0 |

Comparative experiments were done according to the known art methods found in Kato et al. (Biochim. Biophys. Acta 881:415–421, 1986). The Kato prior art method employed the following reactants: 0.1 mM DOPA, 0.2 mM BSA (range tested=0.05–1 mM); and 10 µg Tyrosinase (mushroom tyrosinase from Sigma) (range tested=2–50 :g) in 1 ml of 0.1 mM sodium phosphate buffer pH 7.4. Tubes were incubated for 5 minutes at 37 ° C. An amount of 1 ml of 10% TCA (trichloroacetic acid) was added to precipitate the protein. The composition was incubated for 1 hour at 4° C., followed by centrifugation to obtain precipitate of protein-bound DOPA.

The same series of experiments were conducted as those represented in Tables 3 and 4, except for presence of 1 ml 10% TCA. A precipitate was obtained in all the tubes with colours ranging from white to light pink to light gray. No colour was seen in the supernatants of any of the tubes suggesting that absolutely no soluble melanin was formed.

Irrespective of the concentrations of any of the reactants used, it is the method which determines what sort of melanin would be formed. When 10% TCA is used, there is complete precipitation of all proteins and therefore any protein bound melanin would also be precipitated. The total amount of soluble melanin formed depends on the concentration of DOPA and tyrosinase used but not on the concentration of BSA.

The foregoing description and examples illustrate selected embodiments of the present invention. In light thereof variations and modifications will be suggested to one skilled in the art, all of which are within the spirit and purview of this invention.

What is claimed is:

1. A process for preparing protein-bound melanin and/or peptide-bound melanin, which is soluble in an aqueous solution at pH 2 to 11 and temperature 0° C. to 50° C., comprising reaction of dihydroxyphenylalanine or tyrosine with an oxidant enzyme in an acidic medium in the presence of a protein and/or peptide having a pI of 3–6 and a molecular weight of at least 45,000 Da wherein dihydroxyphenylalanine or tyrosine to oxidant enzyme to the protein and/or peptide in the acidic medium is present in a molar ratio of 1–5:0.0001–0.001:0.01–0.2.

2. A process according to claim 1 wherein the enzyme is a tyrosinase.

3. A process according to claim 2 wherein the source of tyrosinase is *Neurospora crassa* or *mushroom tyrosinase*.

4. A process according to claim 1 wherein the concentration of the protein and/or peptide in the reaction mixture is 1 microM to 1 mM.

5. A process according to claim 1 further comprising in the reaction a metal ion selected from the group consisting of copper, zinc and iron ions.

6. A sunscreen composition comprising:
   (a) 0.1 to 10% by weight of the composition of the soluble protein-bound melanin and/or peptide-bound melanin prepared by the process of claim 1; and
   (b) a cosmetically acceptable vehicle.

7. A colouring and/or flavouring composition for food stuffs comprising:
   (a) 0.01 to 10% by weight of the composition of the soluble protein-bound melanin and/or peptide-bound melanin prepared by the process of claim 1; and
   (b) an edible foodstuff.

8. A skin lightening composition comprising:
   (a) from 0.1 to 10% by weight of the composition of a skin whitening agent; and
   (b) 0.1 to 10% by weight of the composition of a soluble protein-bound melanin and/or peptide-bound melanin prepared by the process of claim 1.

* * * * *